| United States Patent [19] | [11] Patent Number: 4,622,416 |
| Hanes et al. | [45] Date of Patent: Nov. 11, 1986 |

[54] CARBONYLATION OF ALLYLIC ETHERS TO ESTERS

[75] Inventors: Ronnie M. Hanes, Milford; William D. Baugh, Wilmington, both of Ohio

[73] Assignee: National Distillers and Chemical Corporation, New York, N.Y.

[21] Appl. No.: 725,290

[22] Filed: Apr. 19, 1985

[51] Int. Cl.$^4$ .......................... C07C 67/36; C11C 3/04
[52] U.S. Cl. .................. 560/114; 260/410.6; 260/410.9 R; 560/206; 560/207
[58] Field of Search ...................... 260/410.9 C, 410.6; 560/114, 206, 207

[56] References Cited

U.S. PATENT DOCUMENTS

| 2,876,254 | 3/1959 | Jenner et al. | 260/410.9 C |
| 2,963,499 | 12/1960 | Aldridge et al. | 260/410.9 C |
| 3,161,672 | 12/1964 | Zachry et al. | 260/410.9 C |
| 3,367,961 | 2/1968 | Brewbaker | 260/410.9 C |
| 3,427,344 | 2/1969 | Tsju et al. | 260/410.9 C |
| 4,172,087 | 10/1979 | Knifton | 260/410.9 C |
| 4,336,399 | 6/1982 | Isshiki et al. | 560/114 |

OTHER PUBLICATIONS

Tsuji et al, *J. Am. Chem. Soc.*, vol. 86, Oct. 20, 1964, pp. 4350–4353, "Organic Synthesis by Means of Noble Metal Cpdspt" VIII.

*Primary Examiner*—Werren B. Lone
*Attorney, Agent, or Firm*—Kenneth D. Tremain

[57] ABSTRACT

A method is disclosed for the production of esters by reaction of an alkyl acyclic allylic ether such as 8-methoxy-1,6-octadiene with carbon monoxide in the presence of a halide of nickel, cobalt or iron as a catalyst and especially nickel iodide for the production of esters. Carbonylation of 8-methoxy-1,6-octadiene results in the production of methyl-3,8-nonadienoate; 2-(carbomethoxymethyl)-vinylcyclopentane; 2-(carbomethoxymethyl)-6-vinylcyclohexanone and 2-carbomethoxymethylbicyclo(3.3.0)-octan-3-one.

18 Claims, No Drawings

CARBONYLATION OF ALLYLIC ETHERS TO ESTERS

DESCRIPTION

1. Technical Field

The present invention relates to the production of esters by the reaction of allylic ethers with carbon monoxide in the presence of a metal compound as a catalyst.

2. Prior Art

Various U.S. patents teach the carbonylation of unsaturated compounds in the presence of a Group VIII noble metal catalyst such as palladium metal. For example, Scheben, U.S. Pat. No. 3,625,005, discloses a process for the production of unsaturated acyl halides by carbonylating vinylic halides in the presence of a Group VIII noble metal catalyst such as palladium metal, the catalyst optionally containing metals such as gold, silver, copper and the like. Similarly, Jenner, et al., U.S. Pat. No. 2,876,254, also discloses a process for the preparation of esters from olefins, carbon monoxide and alcohols in the presence of a Group VIII noble metal and an alcohol-soluble salt of tin or germanium.

Other U.S. patents teach the production of esters such as Knifton, U.S. Pat. No. 4,172,087, in which a process is disclosed for the preparation of unsaturated aliphatic esters from aliphatic dienes such as butadiene by reacting a diene with carbon monoxide and an alcohol in the presence of a palladium catalyst and an amine base. Group VIII noble metal catalysts are also disclosed for the preparation of esters in a similar manner by Zachry, et al., U.S. Pat. No. 3,161,672; Tsuji, et al., U.S. Pat. No. 3,427,344; Fenton, U.S. Pat. No. 3,652,255; Biale, U.S. Pat. No. 3,530,168 and Brewbaker, U.S. Pat. No. 3,367,961.

All of the above references emphasize the use of a Group VIII noble metal catalyst for the carbonylation reaction. Although metals of this type are effective in promoting carbonylation, their high cost is a principal drawback in employing them and additionally, some catalyst is lost during the reaction. Less expensive catalysts, therefore, would be desirable for promoting the carbonylation reaction, especially for processes that are carried out on an industrial scale. Catalyst loss, although undesirable, would not be as severe an economic problem when compared to replacing Group VIII noble metal catalysts in this reaction.

SUMMARY OF THE INVENTION

Accordingly, it is an object of the present invention to overcome these and other difficulties encountered in the prior art.

It is a further object of the present invention to provide a catalyst for the reaction of an allylic ether with carbon monoxide for the production of acyclic and cyclic esters.

It is a further object of the invention to provide such a catalyst based on a metal from the group consisting of nickel, cobalt and iron and especially nickel.

It is a further object of the present invention to provide such a catalyst based on the halides of nickel, cobalt and iron, especially the halides of nickel, as well as various mixtures of such halides.

These and other objects have been achieved according to the present invention which comprises a method for the production of esters by reacting an allylic ether with carbon monoxide in the presence of a catalytically effective amount of a catalyst based on nickel, cobalt or iron and especially the halides of nickel, cobalt or iron and preferably the halides of nickel as well as mixtures of the aforementioned halides.

DETAILED DESCRIPTION

It has been discovered that the carbonylation of allylic ethers with nickel halides, especially nickel iodide, results in the production of acyclic and cyclic esters. The nickel halide catalysts may comprise a single nickel halide or mixtures of nickel halides. The nickel halides employed preferably comprise nickel iodide, nickel bromide and nickel chloride or mixtures thereof and especially nickel iodide or mixtures of nickel iodide with nickel chloride and/or nickel bromide.

Cobalt halides and iron halides and mixtures thereof may also be employed. The iodides, bromides and chlorides, especially the iodides of cobalt and iron may be used as well as mixtures thereof. The catalyst therefore comprises, in its broadest scope, a halide of nickel, iron or cobalt and various mixtures thereof, whereas the preferred catalyst comprises a nickel halide as well as mixtures of various nickel halides, the most preferred nickel halide comprising nickel iodide.

Various alkyl acyclic allylic ethers (referred to herein as allylic ethers) may be employed as a substrate for the carbonylation reaction, one of the preferred allylic ethers comprising methoxyoctadiene which includes the various isomers thereof and especially 8-methoxyl-1,6-octadiene. In one aspect of this invention, it has been discovered that methoxyoctadiene may be carbonylated in the presence of a nickel halide catalyst such as a catalyst comprising nickel iodide for the production of acyclic esters comprising methyl nonadienoate and cyclic esters comprising 2-(carbomethoxymethyl)-vinylcyclopentane,

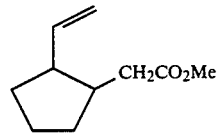

2-(carbomethoxymethyl)-6-vinylcyclohexanone;

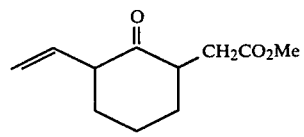

and 2-carbomethoxymethylbicyclo-(3.3.0)-octan-3-one.

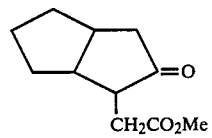

Other allylic ether substrates that may be employed in the carbonylation reaction of the present invention comprise:
methyl allyl ether;
methyl-2-butenyl ether;
methyl 4-methoxyerotonate;
1-methoxy-2-penten-4-one;

1-methoxy-3-hexen-5-one;
ethyl allyl ether;
isopropyl allyl ether;
8-isopropoxy-1,6-octadiene;
1-ethoxy-2-hexene;
1-methoxy-2-hexene;
1-isopropoxy-2-pentene.

Although the foregoing are specific examples of allylic ethers that may be reacted according to the method of the present invention, any ethers may be employed as a substrate and comprise those allylic ethers having up to about 20 carbon atoms and especially those having from about 5 to about 20 carbon atoms. The esters obtained by employing the method of the present invention have from about 6 to about 21 carbon atoms. In addition, the aforesaid ethers may contain up to about 4 olefinically unsaturated positions and especially up to about 2 olefinically unsaturated positions along the acyclic chain. The acyclic esters obtained similarly comprise the alkyl acyclic esters having up to about 21 carbon atoms and especially from about 6 to about 21 carbon atoms and include both the acyclic saturated and unsaturated esters having up to about 4 olefinically unsaturated positions along the acyclic hydrocarbon chain and especially up to about to about 2 of such olefinically unsaturated positions. The acyclic group may be a straight chain or a branched chain.

The alkyl group of either the allylic ether or the esters obtained according to the process of the present invention comprises a lower alkyl group having from 1 to about 6 and especially from 1 to about 4 carbon atoms and may comprise either straight chain or branched chain lower alkyl groups. The methyl ethers and methyl esters are especially preferred.

The nickel catalyst has been found to be especially useful for the carbonylation of the various substrates, especially the methoxyoctadiene substrates. It has been discovered that depending on the halide, the catalyst will have a decreasing order of activity in which nickel iodide has been found to be more active than nickel bromide which in turn is more active than nickel chloride.

The catalyst may be formed by reacting nickel metal with hydrogen iodide, hydrogen bromide or hydrogen chloride or by combining a nickel halide catalyst with a hydrogen halide to form a nickel halide catalyst in which the halogens of the starting nickel halide and the hydrogen halide are exchanged. For example, nickel chloride can be reacted with hydrogen iodide to form nickel iodide. This reaction is especially useful in the recovery of the catalyst which will be described later.

In conducting the reaction, it has been found that the nickel halide catalyst when employed at high pressures is converted to a volatile compound such as nickel carbonyl which is a gas at room temperature and higher temperatures. The volatile nickel compound thus obtained is recycled in one aspect of the invention by reaction with a water solution of sodium hypochlorite whereby the nickel is converted into nickel chloride. Although the nickel chloride may be employed in the subsequent carbonylation reactions, it is preferred to convert the nickel chloride thus obtained to nickel iodide by reacting it with hydrogen iodide as described above.

When the carbonylation reaction of the present invention is conducted at lower pressures, the catalyst remains substantially in solution. For example, at pressures from atmospheric pressure up to about 500 psig and especially at about 350 psig, approximately 85 percent of the catalyst remains in solution whereas at higher pressures the catalyst is volatilized and optionally recovered such as by the method described previously after which it is recycled for subsequent carbonylation reactions.

The catalyst of the present invention may also contain a ligand such as a triphenylphosphine, triphenylstibene or triphenylarsine ligand and the various art known equivalents thereof as set forth by Knifton in U.S. Pat. No. 4,172,087 which is incorporated herein by reference.

The reaction may be conducted at pressures anywhere from atmospheric pressure up to about 5000 psig although where acyclic esters are to be produced, it is preferred to conduct the carbonylation reaction at pressures from greater than 500 up to about 5000 psig; and where cyclic esters are to be produced, it is preferred to conduct the reaction at from atmospheric pressure up to about 500 psig. In either instance, both acyclic esters and cyclic esters are produced simultaneously, the purpose of conducting the reaction at the higher or lower pressures being to favor the production of the acyclic or the cyclic esters. Additionally, by employing the lower pressure ranges, the volatilization of the catalyst is substantially minimized.

It is preferred to conduct the reaction in a solvent, especially weakly coordinating solvents such as the nitriles. Nitrile solvents that may be employed in this respect comprise acetonitrile, butyronitrile, adiponitrile, benzonitrile and the art known equivalents thereof. Additionally, amide solvents may be employed such as dimethylformamide (DMF), acetamide and the art known equivalents thereof. Other solvents that may be used in this regard include sulfolane and dimethylsulfoxide (DMSO).

The catalyst is employed in a catalytically effective amount i.e. that amount which will aid in the carbonylation of the substrate to an ester. It has been found that anywhere from about ½ to about 5 mole percent of catalyst based on the molar amount of substrate is effective for promoting the carbonylation reaction.

Additionally, the carbonylation reaction may be conducted at temperatures anywhere from about 50° C. to about 200° C. and especially from about 125° C. to about 175° C.

The following examples are illustrative and relate to the carbonylation of 8-methoxy-1,6-octadiene. Esters were formed comprising methyl-3,8-nonadienoate (I); 2-(carbomethoxymethyl)-vinylcyclopentane (II); 2-(carbomethoxymethyl)-6-vinylcyclohexanone (III); and 2-carbomethoxymethylbicyclo-(3.3.0)-octan-3-one (IV) referred throughout the examples as compounds I, II, III and IV respectively.

EXAMPLE 1

Four glass-lined 71 ml Parr bombs were charged as follows:

|  | Example 1a | Example 1b | Example 1c | Example 1d |
|---|---|---|---|---|
| 8 methoxy-1,6-octadiene | 5.0 ml | 5.0 ml | 5.0 ml | 5.0 ml |
| NiI$_2$ | 0.5 g | 0.5 g | 0.1 g | 0.1 g |
| Ph$_3$As | 1.0 g | 1.0 g | 0.5 g | 0.5 g |
| Water |  | 0.2 ml |  | 0.2 ml |

-continued

|  | Example 1a | Example 1b | Example 1c | Example 1d |
|---|---|---|---|---|
| Conversion | 35.1% | 50.3% | 2.0% | 1.7% |

The bombs were pressured to 2500 psig with carbon monoxide and heated in a shaker bath at 125° C. for 6 hours. Afterwards the contents of the bombs were analyzed by means of a Silar GLC column.

In all instances, esters I, II, III and IV were obtained. The data show that nickel iodide optionally containing a triphenylarsine ligand is an effective catalyst for the carbonylation of methoxyoctadiene and that water may also be employed in the reaction.

EXAMPLE 2

The procedure of Example 1 was substantially followed employing the following reactants:

|  | Example 2a | Example 2b | Example 2c | Example 2d |
|---|---|---|---|---|
| 8 methoxy-1,6-octadiene | 5.0 ml | 5.0 ml | 5.0 ml | 5.0 ml |
| acetonitrile | 5.0 ml | 2.0 ml |  |  |
| benzonitrile |  |  | 5.0 ml |  |
| adiponitrile |  |  |  | 5.0 ml |
| $NiI_2$ | 1.0 g | 1.0 g | 1.0 g | 1.0 g |
| Conversion | 96.7% | 74.4% | 87.8% | 98.1% |
| Selectivity (I) | 90.8% | 90.6% | 93.2% | 79.8% |
| Selectivity (II), (III) and (IV) | 9.2% | 9.4% | 6.8% | 10.2% |

The reactions were run at a carbon monoxide initial pressure of 2500 psig for 3 hours at 150° C. The contents of each of the bombs were analyzed as in Example 1, the results of which are given in the above table.

The foregoing data indicate that when acetonitrile is reduced with respect to the ether that conversion decreases.

EXAMPLE 3

The procedure of Example 1 was substantially followed by charging four 71 ml glass-lined Parr bombs with 5.0 ml , 8-methoxy-1,6-octadiene, 2.0 ml adiponitrile and 1.0 g $NiI_2$ at pressures of 350 psig, 500 psig, 1000 psig and 1500 psig of carbon monoxide respectively. The bombs were then placed in a shaker bath and heated at 150° C. for six hours and the contents analyzed as in Example 1 for conversion and selectivities to esters I, II, III and IV as well as the nickel component of the nickel iodide catalyst.

At 350 psig carbon monoxide pressure, conversions of 96.2% were obtained along with selectivities of 30% of a mixture of esters I and II (most of which consisted of ester I) and 47.4% of a mixture of esters II and III.

At 500 psig carbon monoxide, 161 mg or 86% of the nickel originally charged to the reaction remained and conversions of 100% were obtained. Selectivities of 12% of ester I, 19.1% of ester II and 45.2% of a mixture of esters II and III were obtained.

At 1000 psig carbon monoxide pressure, 55 mg or 29% nickel, based on the nickel iodide catalyst originally charged, remained after the reaction was stopped. The conversion was 100% with selectivities to ester I of 63.8%, ester II of 17.1% and a mixture of esters III and IV of 18.1% were obtained.

At 1500 psig carbon monoxide, 21 mg or 11% nickel, based on the original nickel iodide catalyst charged, remained whereas conversions of 100% were obtained along with selectivities to ester I of 75.5%, ester II of 13.3% and a mixture of esters III and IV of 11.2%.

The foregoing data indicate that at lower pressures, the production of esters II, III and IV are favored whereas an increase in pressure favors the production of ester I with the attendant loss of nickel iodide catalyst. The data suggest that the nickel catalyst is converted to a volatile material such as nickel carbonyl at the higher pressures.

EXAMPLE 4

A 300 ml glass-lined stirred autoclave was charged with 8-methoxy-1,6-octadiene, 50.0 ml ; acetonitrile, 50.0 ml ; and $NiI_2$, 5.0 g and pressured up to 1500 psig with carbon monoxide. The reaction was conducted over a 5½ hour time period during which the carbon monoxide pressure was maintained at a constant pressure of 1500 psig by addition of carbon monoxide gas to the autoclave through a pressure regulator valve. The autoclave was brought to 150° C. in about ½ hour's time. Seven 3 ml samples of the liquid reactor contents were taken at ½ hour intervals starting 1 hour after the reaction was initiated.

The samples were analyzed in the same manner as Example 1, the results of which are given below:

|  | Sample |  |  |  |  |  |  |
|---|---|---|---|---|---|---|---|
|  | 1 | 2 | 3 | 4 | 5 | 6 | 7 |
| Conversion | 21.9% | 43.7% | 54.3% | 56.1% | 57.4% | 58.9% | 59.7% |
| Selectivity I | 71.1% | 78.4% | 82.0% | 83.3% | 81.5% | 80.1% | 80.9% |
| Selectivity II, III and IV | 28.9% | 21.6% | 18.0% | 16.7% | 18.5% | 19.9% | 19.1% |

At the end of the reaction, the liquid contents of the reactor were analyzed, and it was found that a conversion of 58.1% was obtained with selectivities to ester I of 85.0% and a mixture of esters II, III and IV of 15%.

The foregoing data show that conversion levels off at about 1½ hours to 2 hours after the reaction was initiated, indicating that catalyst activity changed at about this time and further indicating the catalyst was volatilized. Additionally, the foregoing data show that the higher reaction pressures favor the production of ester I.

Methyl-3,8-nonadienoate may be converted to a monocarboxylic acid by reaction with a dilute mineral acid such as hydrochloric acid. The monocarboxylic acid thus produced may be reacted with a long chain monohydric alcohol such as lauryl alcohol or any monohydric acyclic alcohol having from about 8 to about 20 carbon atoms and the various isomers thereof to produce an ester which may be employed as a plasticizer for various synthetic resins such as polyvinylchloride or polyvinylchloride-polyvinylacetate co-polymers or as a lubricant for reducing friction between two surfaces, such as metal or plastic surfaces.

2-(carbomethoxymethyl)-vinylcyclopentane can be polymerized through the vinyl group with vinyl monomers such as vinylchloride, vinylacetate or mixtures thereof or with styrene, acrylic acid, acrylic acid esters, methacrylic acid, methacrylic acid esters, butadiene or acrylonitrile and various mixtures thereof to form synthetic resinous materials that are useful as molding compositions for the formation of plastic films, containers or solid members requiring structural integrity. Additionally, 2-(carbomethoxymethyl)-vinylcyclopentane may be reacted with a dilute mineral acid in the same manner as methyl-3,8-nonadienoate to form a monocarboxylic acid which in turn may be reacted with a long chain alcohol to form an ester useful as a plasticizer or a lubricant.

2-(carbomethoxymethyl)-vinylcyclopentane may also be oxidized in an art-known manner to form a dicarboxylic acid which may be reacted with a diol or polyol to form a polyester resin which is useful in the formation of surface coatings, or polyurethanes, for the manufacture of plastic films or the manufacture of reinforced fiber glass structures such as automobile bodies.

When the 2-(carbomethoxymethyl)-vinylcyclopentane is converted into a monocarboxylic acid by reaction with a mineral acid or by other means well known in the art, the monocarboxylic acid obtained may also be incorporated into a polyester resin as a terminal ester moiety and thereby provide a vinyl group along the polyester chain for subsequent cross-linking with styrene monomer by methods that are well known in the polyester art.

The 2-(carbomethoxymethyl)-6-vinylcyclohexanone is used in the same way as the 2-(carbomethoxymethyl)-vinylcyclopentane as described above.

The 2-carbomethoxymethylbicyclo-(3.3.0)-octan-3-one is subjected to oxidative ring cleavage in an art-known manner to form either a dicarboxylic ketone or a tricarboxylic acid, both the dicarboxylic ketone and the tricarboxylic acid being useful for reaction with long chain monohydric alcohols (as that term is used hereinabove) for the formation of diesters or triesters which find utility as lubricants to reduce friction between surfaces and as a plasticizer for vinyl resins.

Although the invention has been described by reference to some embodiments, it is not intended that the novel process and compositions be limited thereby but that various modifications thereof are intended to be included as falling within the spirit and the broad scope of the foregoing disclosure and the following claims.

What is claimed is:

1. A method for the production of esters comprising reacting an allylic ether with carbon monoxide in the presence of a catalytically effective amount of a compound selected from the group of nickel halides, cobalt halides or iron halides or mixtures thereof to obtain acyclic and cyclic esters where said allylic ether has from about 5 to about 20 carbon atoms and said ester has from about 6 to about 21 carbon atoms, said reaction being conducted at temperatures from about 50° C. to about 200° C. and at pressures from atmospheric pressure up to about 5000 psig.

2. The method of claim 1 where said catalyst comprises a nickel halide and mixtures of nickel halides.

3. The method of claim 2 where said allylic ether comprises an alkoxy alkadiene.

4. The method of claim 2 where said halides of nickel are selected from chlorides, bromides or iodides of nickel and mixtures thereof.

5. The method of claim 4 where said allylic ether comprises a lower alkoxy alkadiene having from 5 carbon atoms to about 20 carbon atoms.

6. The method of claim 5 where said allylic ether comprises methoxyoctadiene.

7. The method of claim 2 where said catalyst is dissolved in a solvent comprising an organic nitrile.

8. The method of claim 7 where said nitrile comprises a member selected from the group, acetonitrile, butyronitrile, adiponitrile, benzonitrile and mixtures thereof.

9. The method of claim 2 where said catalyst is dissolved in a solvent selected from dimethylformamide, sulfolane and dimethylsulfoxide.

10. The method of claim 6 where said reaction is conducted at temperatures of about 50° C. to about 200° C. and at pressures from greater than 500 psig to about 5000 psig to increase the yield of acyclic esters.

11. The method of claim 6 where said reaction is conducted at temperatures from about 50° C. to about 200° C. and at pressures from about atmospheric pressure to about 500 psig to increase the yield of cyclic esters.

12. The method for the production of methylnonadeienoate, 2-(carbomethoxymethyl)-vinylcyclopentane, 2-(carbomethoxymethyl-6-vinylcyclohexanone and 2-carbomethoxymethylbicyclo-(3.3.0)-octan-3-one comprising reacting methoxyoctadiene with carbon monoxide in the presence of a catalyically effective amount of a nickel halide catalyst where said reaction is conducted at temperatures of from about 50° C. to about 200° C. at pressures from atmospheric pressure up to about 5000 psig.

13. The method of claim 12 where said methoxyoctadiene comprises 8-methoxy-1,6-octadiene.

14. The method of claim 12 where said nickel halide catalyst is selected from nickel chloride, nickel bromide or nickel iodide and mixtures thereof.

15. The method of claim 12 where said catalyst comprises nickel iodide.

16. The method of claim 14 where said catalyst is dissolved in a solvent comprising an organo nitrile.

17. The method of claim 16 were said organo nitrile is selected from the group, acetonitrile, butyronitrile, adiponitrile, benzonitrile and mixtures thereof.

18. The method of claim 14 where said catalyst is dissolved in a solvent selected from the group comprising dimethylformamide, sulfolane and dimethylsulfoxide.

* * * * *